United States Patent
Ponsky et al.

(10) Patent No.: US 10,070,978 B2
(45) Date of Patent: Sep. 11, 2018

(54) STENT PUSHER ASSEMBLY

(71) Applicant: UNIVERSITY HOSPITALS HEALTH SYSTEMS, INC., Cleveland, OH (US)

(72) Inventors: Lee E. Ponsky, Moreland Hills, OH (US); Dean Secrest, Concord, OH (US)

(73) Assignee: University Hospitals Cleveland Medical Center, Cleveland, OH (US)

( * ) Notice: Subject to any disclaimer, the term of this patent is extended or adjusted under 35 U.S.C. 154(b) by 0 days.

(21) Appl. No.: 15/710,296

(22) Filed: Sep. 20, 2017

(65) Prior Publication Data

US 2018/0008441 A1   Jan. 11, 2018

Related U.S. Application Data

(63) Continuation of application No. 14/406,387, filed as application No. PCT/US2013/044987 on Jun. 10, 2013.

(Continued)

(51) Int. Cl.
| | |
|---|---|
| *A61F 2/04* | (2013.01) |
| *A61F 2/95* | (2013.01) |
| *A61F 2/82* | (2013.01) |
| *A61M 27/00* | (2006.01) |
| *A61M 25/00* | (2006.01) |

(52) U.S. Cl.
CPC ............... *A61F 2/95* (2013.01); *A61F 2/042* (2013.01); *A61F 2/82* (2013.01); *A61M 27/008* (2013.01); *A61F 2002/047* (2013.01); *A61F 2002/048* (2013.01); *A61F 2220/005* (2013.01); *A61F 2220/0008* (2013.01); *A61F 2220/0075* (2013.01); *A61F 2230/0006* (2013.01); *A61F 2230/0013* (2013.01); *A61F 2230/0041* (2013.01); *A61F 2230/0069* (2013.01); *A61F 2250/0006* (2013.01); *A61F 2250/006* (2013.01); *A61F 2250/0014* (2013.01); *A61F 2250/0018* (2013.01); *A61F 2250/0019* (2013.01); *A61F 2250/0029* (2013.01); *A61F 2250/0036* (2013.01);
(Continued)

(58) Field of Classification Search
CPC ...... A61F 2002/048; A61F 2002/2002; A61M 27/008
See application file for complete search history.

(56) References Cited

U.S. PATENT DOCUMENTS

| | | |
|---|---|---|
| 4,713,049 A | 12/1987 | Carter |
| 4,913,683 A | 4/1990 | Gregory |

(Continued)

FOREIGN PATENT DOCUMENTS

| | | |
|---|---|---|
| EP | 0365269 | 4/1990 |
| WO | 2005096991 | 10/2005 |
| WO | 2007027830 | 3/2007 |

OTHER PUBLICATIONS

International Search Report for corresponding Patent Application No. PCT/US2013/044987, dated Sep. 3, 2013.

*Primary Examiner* — Andrew Iwamaye
(74) *Attorney, Agent, or Firm* — Tucker Ellis LLP (57) ABSTRACT

Provided is a stent pusher assembly for positioning a ureteral stent, the stent pusher assembly having an inner and outer stent pusher. The stent pusher assembly positions the ureteral stent in a patient's kidney and bladder without a bladder fixing portion of the stent entering a ureteral passage-way, thereby minimizing irritation to the patient.

8 Claims, 10 Drawing Sheets

Related U.S. Application Data (60) Provisional application No. 61/657,238, filed on Jun. 8, 2012.

(52) U.S. Cl.
CPC ............... *A61F 2250/0039* (2013.01); *A61F 2250/0098* (2013.01); *A61M 2025/0004* (2013.01)

(56) References Cited

U.S. PATENT DOCUMENTS

| | | |
|---|---|---|
| 4,931,037 A | 6/1990 | Wellerman |
| 4,957,479 A | 9/1990 | Roemer |
| 5,141,502 A | 8/1992 | MacAluso |
| 5,322,501 A | 6/1994 | Mahmud-Durrani |
| 5,599,291 A | 2/1997 | Balbierz |
| 6,248,100 B1 | 6/2001 | de Toledo |
| 6,258,098 B1 | 7/2001 | Taylor |
| 7,041,139 B2 | 5/2006 | Bluni |

STENT PUSHER ASSEMBLY

RELATED APPLICATIONS

This application is a continuation of U.S. application Ser. No. 14/406,387, filed Dec. 8, 2014, which is a national phase application of International Application No. PCT/US2013/044987, filed Jun. 10, 2013, which claims the benefit of U.S. Provisional Application No. 61/657,238 filed Jun. 8, 2012, which are hereby incorporated herein by reference.

FIELD OF INVENTION

The present invention relates generally to implantable medical devices, and more particularly to a stent insertion assembly for inserting a ureteral stents.

BACKGROUND

The urinary tract has a pair of kidneys that connect to a bladder by ureteral passageways, and a urethra that extends from the bladder to the exterior of a patient. Urine is made by the kidneys, passed through the ureteral passageway, stored in the bladder and ultimately voided from the urethra. A urinary sphincter is positioned around the urethra near the base of the bladder to control the flow of urine from the bladder.

The ureteral passageways normally allow urine to pass from the kidney to the bladder by peristalsis. When the bladder fills with urine, the bladder compresses a segment of the ureteral passageway that passes through a wall of the bladder to prevent urine from going backwards from the bladder into the kidney. These passageways can become blocked by tumors or kidney stones thereby preventing normal urine flow, and the resulting high pressure within the kidneys can cause pain to the patient. To reopen a blocked ureteral passageway, a ureteral stent can be positioned in the patient. The stent holds the blockage in the passageway open, for example to allow a small kidney stone to pass. This enables urine to flow from the kidney into the bladder, reduces kidney pressure, and reduces pain of the patient.

SUMMARY OF INVENTION

The present invention provides a stent pusher assembly for positioning a ureteral stent, the stent pusher assembly having an inner and outer stent pusher. The stent pusher assembly positions the ureteral stent in a patient's kidney and bladder without a bladder fixing portion of the stent entering a ureteral passageway, thereby minimizing irritation to the patient.

According to one aspect of the invention, a method for positioning a ureteral stent in a kidney, ureteral passageway and bladder of a patient using a stent pusher assembly is provided. The stent pusher assembly has an inner and outer pusher and the ureteral stent includes a bladder portion configured to be positioned in the bladder, a kidney portion configured to be positioned in the kidney and the ureteral passageway, and at least one tether coupled to the bladder portion and the kidney portion. The method includes advancing a guidewire into the bladder, the ureteral passageway and the kidney, advancing the kidney portion and bladder portion over the guidewire, advancing the outer pusher over the guidewire, advancing the outer pusher along the guidewire until a second end of the outer pusher abuts a first end of the bladder portion, advancing the outer pusher towards the kidney to advance the bladder portion and kidney portion until the kidney portion is substantially positioned in the ureteral passageway, advancing the inner pusher over the guidewire, through a lumen of the outer pusher and through a lumen of the bladder portion until a second end of the inner pusher abuts a second end of the kidney portion, and advancing the inner pusher towards the kidney to advance the kidney portion such that the second end of the kidney portion is disposed in the ureteral passageway and a first end of the kidney portion is disposed in the kidney.

The kidney portion and bladder portion are in respective restrained shapes when the guidewire extends through the kidney portion and bladder portion.

The method further includes withdrawing the guidewire from the first end of the kidney portion to allow the first end to move to its unrestrained shape to secure the kidney portion in the kidney, and withdrawing the guidewire, inner pusher and outer pusher from the bladder portion to allow the bladder portion to move to its unrestrained shape to prevent the bladder portion from migrating into the ureteral passageway.

Advancing the outer pusher towards the kidney until the kidney portion is substantially positioned in the ureteral passageway includes advancing the outer pusher until a portion of the kidney portion is positioned in the bladder and a majority of the kidney portion is positioned in the ureteral passageway.

The outer pusher has an axial length less than an axial length of the inner pusher.

An outer diameter of the inner pusher is equal to or greater than an outer diameter of the kidney portion to allow the inner pusher to advance the kidney portion without entering a lumen of the kidney portion.

An inner diameter of the bladder portion is greater than an outer diameter of the kidney portion to allow the inner pusher having an outer diameter equal to or greater than the outer diameter of the kidney portion to be advanced through the bladder portion.

According to another aspect of the invention, a pusher assembly for positioning a ureteral stent in a kidney, ureteral passageway and bladder of a patient is provided. The pusher assembly includes an inner stent pusher including a body having a lumen and a handle member coupled to a first end of the body, and an outer stent pusher including a body having a lumen and a handle member coupler to a first end of the body, wherein the body of the inner stent pusher has an axial length greater than an axial length of the body of the outer stent pusher, and wherein the body of the inner stent pusher has an outer diameter that is less than an inner diameter of the body of the outer stent pusher to allow the inner stent pusher to move through the lumen of the outer stent pusher during placement of the ureteral stent.

The handle member of the inner stent pusher acts as a stop to prevent the first end of the body of the inner stent pusher from entering the lumen of the outer stent pusher during placement of the ureteral stent.

The pusher assembly further includes a guidewire configured to extend through the lumen in the inner stent pusher.

The pusher assembly is provided in combination with the ureteral stent.

The ureteral stent includes a bladder portion configured to be positioned in the bladder, a kidney portion configured to be positioned in the kidney and the ureteral passageway, and at least one tether coupled to the bladder portion and the kidney portion.

The bladder portion is biased in an unrestrained position.

The guidewire is configured to extend through the bladder portion during placement of the stent to place the bladder portion in a restrained position.

The bladder portion is substantially straight when in the restrained position and curved when in the unrestrained position.

The kidney portion has a resilient fixing portion configured to be positioned in the kidney and a ureter portion configured to be positioned in the kidney and the ureteral passageway to place the ureteral passageway in an open state, the resilient fixing portion being biased in an unrestrained position.

The guidewire is configured to extend through the kidney portion during placement of the stent to place the resilient fixing portion in a restrained position.

The resilient fixing portion is substantially straight when in the restrained position and curved when in the unrestrained position The bladder portion and the fixing portion are movable between a restrained position when being positioned in the bladder and kidney by the pusher assembly and the unrestrained position when positioned in the bladder and kidney.

An outer diameter of the inner stent pusher is equal to or greater than an outer diameter of the kidney portion to allow the inner pusher to advance the kidney portion without entering a lumen of the kidney portion.

An inner diameter of the bladder portion is greater than an outer diameter of the kidney portion to allow the inner pusher having an outer diameter equal to or greater than the outer diameter of the kidney portion to be advanced through the bladder portion.

The foregoing and other features of the invention are hereinafter described in greater detail with reference to the accompanying drawings.

DETAILED DESCRIPTION

The principles of the present application have particular application to ureteral stent pusher assemblies for positioning ureteral stents and thus will be described below chiefly in this context. It will, of course, be appreciated and also understood that the principles of the application may be useful in other medical applications, for example for the placement of other stents.

Figure 1:
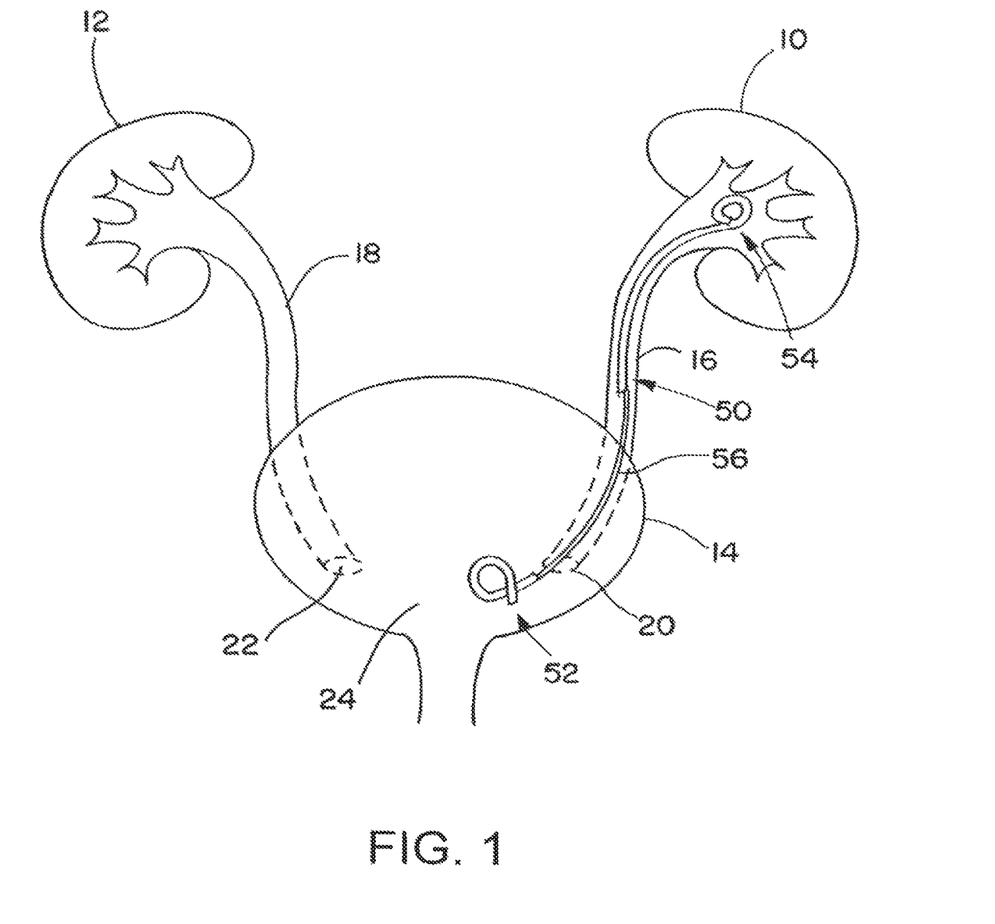
FIG. 1 is a schematic view of an exemplary stent positioned in a patient.

Referring now in detail to the drawings and initially to FIG. 1, a pair of kidneys 10 and 12 and a bladder 14 of a patient are shown. The kidneys 10 and 12 are connected to the bladder 14 by respective ureteral passageways 16 and 18. The ureteral passageways 16 and 18 each include a portion extending into the bladder 14 that moves from an uncompressed state to compressed state and in a normal state only allows urine to pass from the kidneys 10 and 12 to the bladder 14 with the help of peristalsis of the ureter. When one of the passageways 16 and 18 becomes blocked, for example by swelling near one of the kidneys 10 and 12 or blockage from a kidney or ureteral stone, a ureteral stent may be positioned in the kidney 10, 12, ureteral passageway 16, 18 and bladder 14 to assist in opening the passageway 16, 18 to aid in the flow of urine. The ureteral stent may be any suitable ureteral stent, such as the type disclosed in U.S. Patent Application No. 61/657,228, which is hereby incorporated herein by reference.

Figure 2:
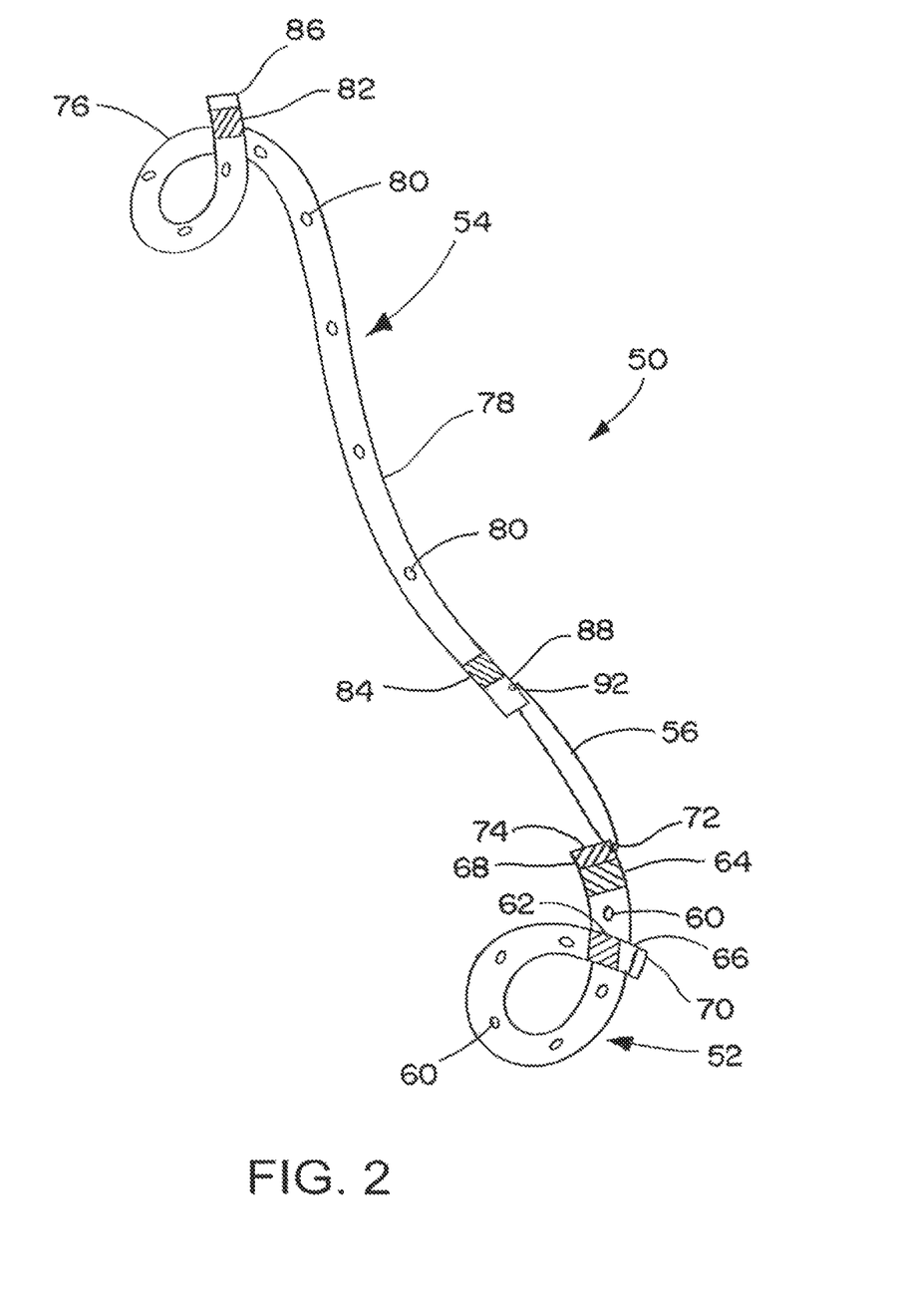
FIG. 2 is a schematic view of the exemplary stent of FIG. 1.

Turning now to FIG. 2, the ureteral stent, referred to herein by reference numeral 50, includes a bladder portion 52 configured to be positioned in the bladder 14, a kidney portion 54 configured to be positioned in the kidney 10 and ureteral passageway 16, and one or more tethers 56 coupling the bladder portion 52 to the kidney portion 54. When in position in the bladder 14 the bladder portion 52 is in an unrestrained shape. When unrestrained the bladder portion 52 is a flexible tube in the form of a flexible loop to prevent the bladder portion 52 from migrating into the ureteral passageway. When being positioned using a pusher assembly, the bladder portion 52 is in a substantially straightened restrained shape.

The bladder portion 52 includes one or more openings 60 in a wall of the bladder portion 52 that allow fluid to flow in/out of the bladder portion 52. The bladder portion 52 also includes at least one radiopaque element, and in the Illustrated embodiment radiopaque bands 62 and 64 near first and second ends 66 and 68 of the bladder portion 52, respectively. The bladder portion 52 additionally includes a tip or ring 70 at the first end 66 having a stiffness greater than a stiffness of the rest of the bladder portion 52 to assist in the insertion of the stent 50, as will be discussed below.

Similar to the bladder portion 52, the kidney portion 54 has a resilient fixing portion 76 that when in position in the kidney 10 is in an unrestrained shape. When unrestrained the resilient fixing portion 76 is a flexible tube in the form of a flexible loop to secure the kidney portion 54 in the kidney 10. When being positioned using the pusher assembly, the kidney portion 54 is in a substantially straightened restrained shape.

The kidney portion 54 also has a ureter portion 78, which may be a flexible tubular portion, configured to extend from the resilient fixing portion 76 in the kidney 10 into the ureteral passageway 16 to keep the passageway open, for example when there is swelling between the kidney and passageway. The kidney portion 54 also includes one or more openings 80 in a wall of the kidney portion that allow fluid to flow to flow in/out of the kidney portion, and at least one radiopaque element such as radiopaque bands 82 and 84 near first and second ends 86 and 88 of the kidney portion, respectively.

As noted above, the bladder portion 52 and kidney portion 54 are coupled together by one or more tethers 56. The tethers have a thin flexible cross-section such that the ureter muscles at the ureter opening 20 can clamp around the tethers and create a urine tight seal. The tethers may be any suitable tether, such as a suitable suture made of cotton, a polymer such as nylon, etc. As shown in FIGS. 1 and 2, the tethers 56 are coupled to the second end 68 of the bladder portion and the second end 88 of the kidney portion in any suitable manner, for example by adhesive, knotting, etc. When the stent 50 is positioned in the body of the patient, the one or more tethers 56 extend from the ureteral passageway 16, through the ureter orifice 20 and into the bladder 14.

Figure 3:
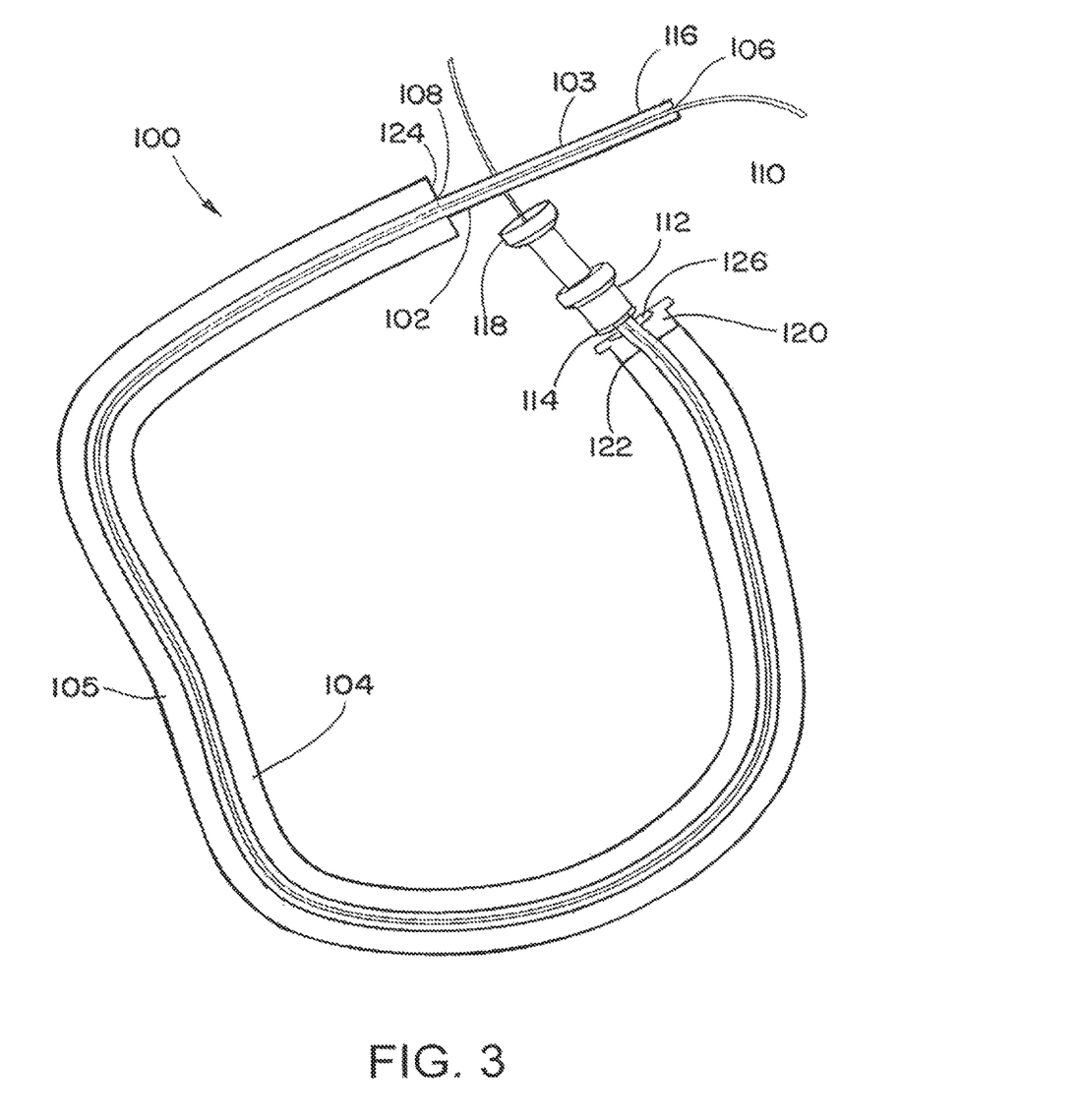
FIG. 3 is a fragmentary cross-sectional view of an exemplary stent pusher assembly and a guidewire according to the invention.

To position the ureteral stent 50, an exemplary stent pusher assembly 100 is provided. As shown in FIG. 3, the stent pusher assembly 100 includes an inner stent pusher 102 and an outer stent pusher 104 surrounding the inner stent pusher. In the illustrated embodiment, the inner stent pusher 102 is concentric with the outer stent pusher 104, although it will be appreciated that the inner stent pusher 102 may be disposed in the outer stent pusher 104 in any suitable manner. The inner and outer stent pushers 102 and 104 may include radiopaque elements along their length to assist an operator in positioning the stent 50, and/or tracking markers along their length.

The inner and outer stent pushers 102 and 104 each have body 103 and 105 having a lumen 106, 108 extending respectively through the bodies 103 and 105. The bodies 103 and 105 of the inner and outer stent pushers 102 and 104 may be tubular members, although it will be appreciated that the bodies of the inner and outer stent pushers may have any suitable shape and may have different shapes from one another.

The body 103 of the inner stent pusher 102 has an axial length greater than an axial length of the body 105 of the outer stent pusher 104, and the body 103 is sized such that an outer diameter is less than an inner diameter of the body 105 of the outer stent pusher 104 to allow the inner stent pusher 102 to move through the outer stent pusher 104 during placement of the stent 50. The body 103 of the inner stent pusher 102 is also sized such that its inner diameter is greater than a diameter of a guidewire 110, which may be any suitable guidewire, to allow the guidewire 110 to move through to the inner stent pusher 102 during placement of the stent 50.

The inner stent pusher 102 also includes a handle member 112 coupled to a first end 114 of a body 103 of the inner stent pusher 102. The handle member 112, which remains outside the patient, acts as a stop to prevent the first end 114 of the body 103 from entering the outer stent pusher 104. The handle member 112 is coupled to the body 103 in any suitable manner, such as adhesive, and may be made of any suitable material, such as plastic. Alternatively, the handle member 112 may be integrally formed with the body 103. To allow the guidewire 110 to extend out of the first end 114 of the body 103 of the inner stent pusher 102, the handle member 112 includes a through-hole 118 having a diameter equal to or greater than the inner diameter of the body 103.

Similar to the inner stent pusher 102, the outer stent pusher 104 includes a handle member 120 coupled to a first end 122 of the body 105 of the outer stent pusher 104. The handle member 120, which remains outside the patient, acts as a stop to prevent the first end 122 from entering the patient. The handle member 120 is coupled to the first end 122 of the body 105 in any suitable manner, such as adhesive, and may be made of any suitable material, such as plastic. Alternatively, the handle member 120 may be integrally formed with the body 105. To allow the guidewire 110 and inner stent pusher 102 to extend out of the first end 122 of body 105, the handle member 120 includes a through-hole 126 having a diameter equal to or greater than the inner diameter of the body 105. Additionally, the handle members 112 and 120 include coupling portions, such as male and female luer lock members, to allow the handle members to be coupled together.

Figure 4:
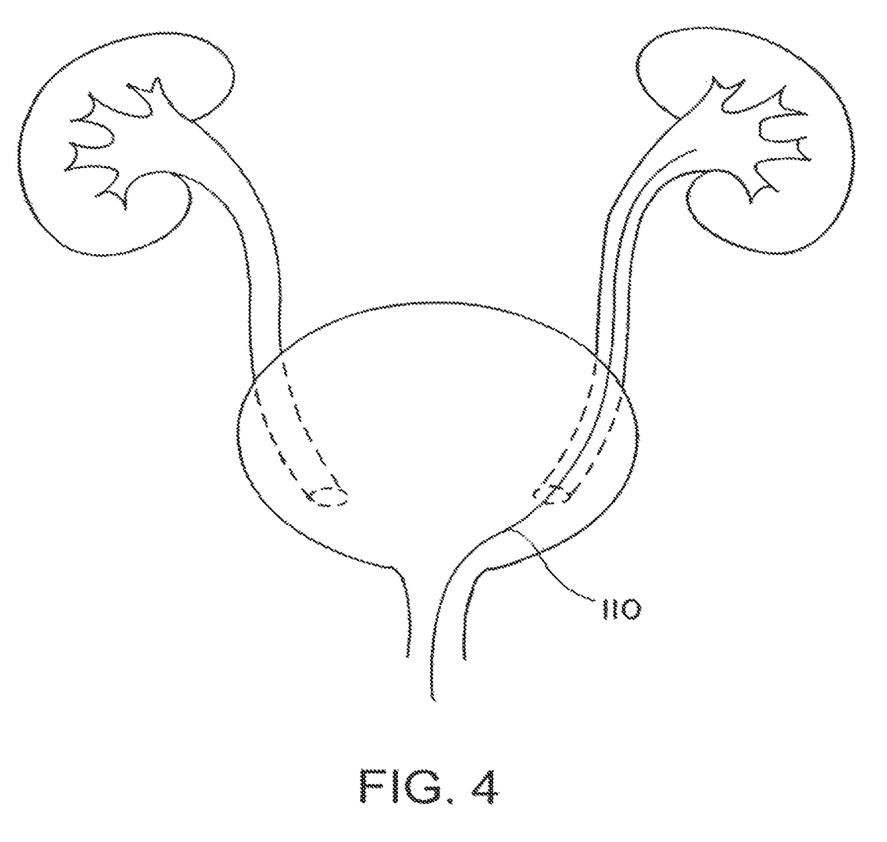
FIG. 4 is a schematic view of a guidewire being inserted into the patient.
Figure 5:
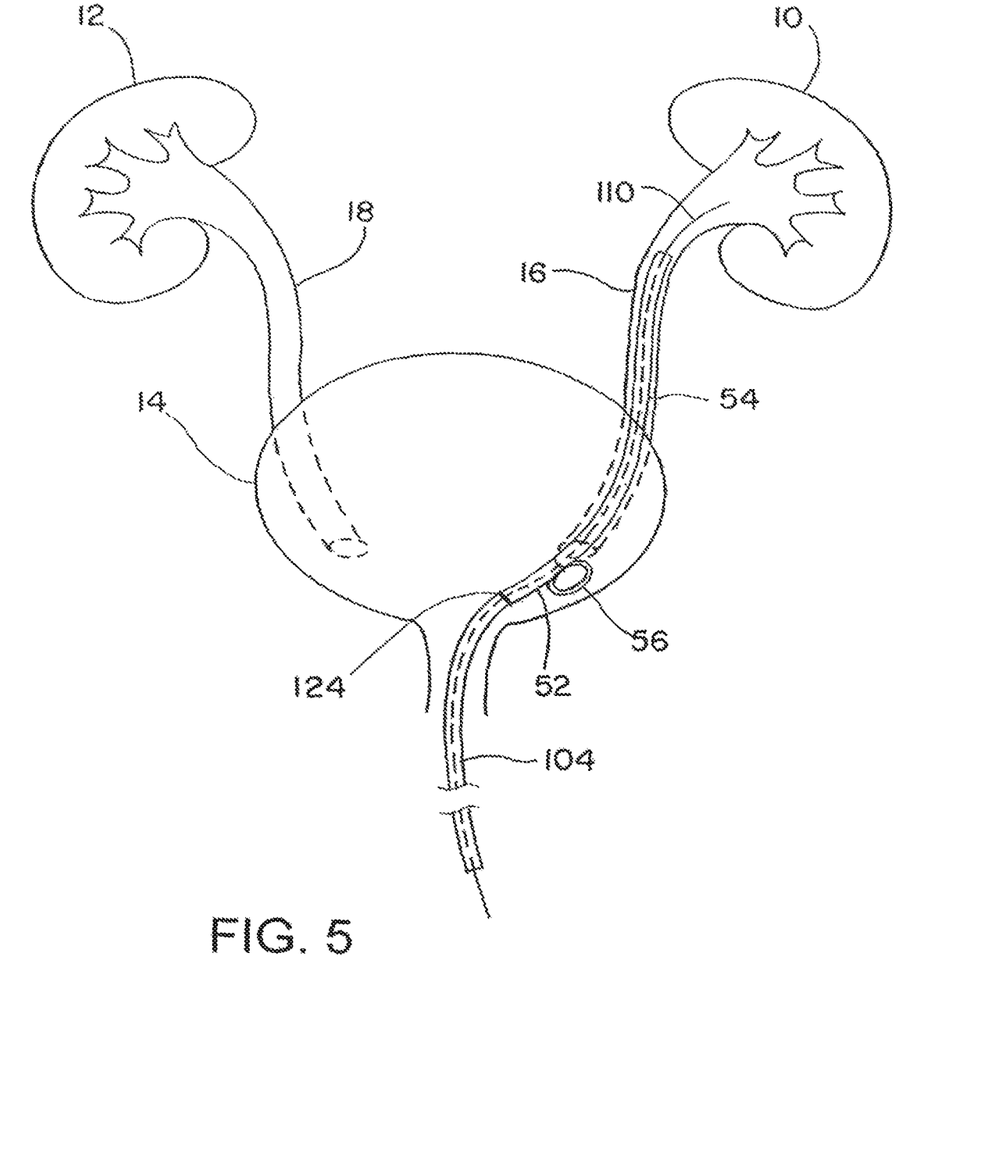
FIG. 5 is a schematic view of the stent assembly being positioned in the patient by the stent pusher assembly.

Referring now to FIGS. 4-7A, an exemplary method of delivering the stent 50 using the pusher assembly 100 will be described in detail. As shown in FIG. 4, the method begins with the guidewire 110 being inserted through the bladder 14, into the ureteral passageway 16 and into the kidney 10. Then, the kidney portion 54 and bladder portion 52 of the stent 50 are advanced over the guidewire 110 outside the patient. It will be appreciated, however, that the kidney portion 52 and the bladder portion 54 can be advanced over the guidewire 110 prior to the guidewire 110 being positioned. Next, the outer stent pusher 104 is advanced over and along the guidewire 110 until a second end 124 of the outer stent pusher 104 abuts the tip 70 at the first end 66 of the bladder portion 52. As the outer stent pusher 104 is advanced, the second end 124 abuts the tip 70 at the first end 66 and the second end 68 of the bladder portion 52 abuts the second end 88 of the kidney portion 54 as shown in FIG. 5.

Figure 6:
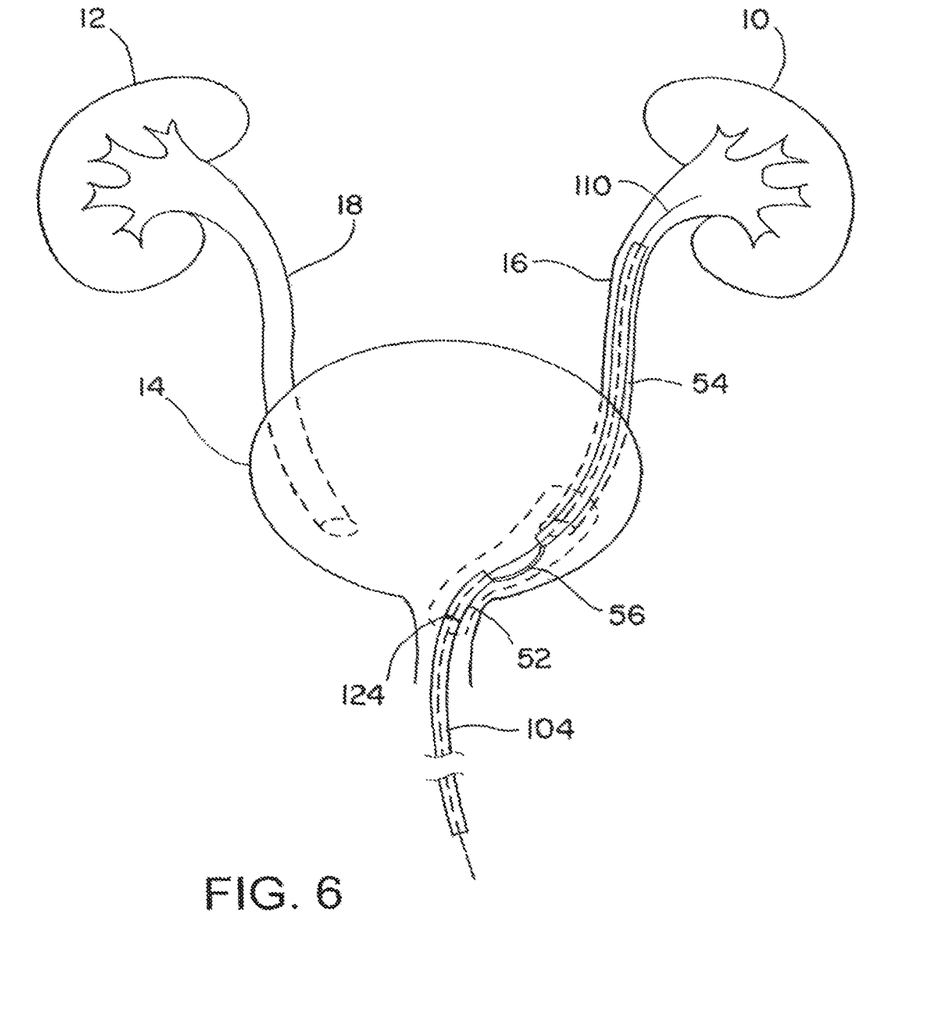
FIG. 6 is another schematic view of the stent assembly being positioned in the patient by the stent pusher assembly.
Figure 6A:
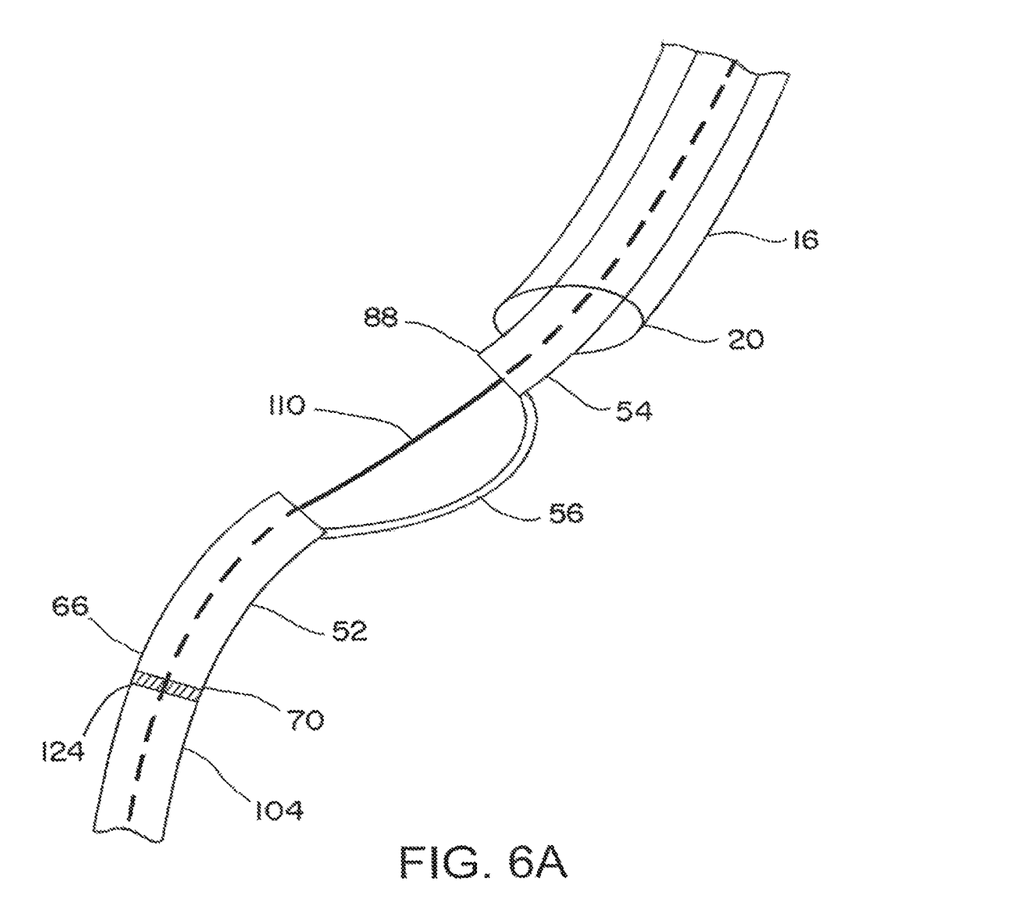
FIG. 6A is a schematic view of a blown-up portion of FIG. 6.

The outer stent pusher 104 is advanced into the patient, thereby advancing the stent 50 into the patient until the bladder portion 52 is positioned or substantially positioned in the bladder 14 and the kidney portion 54 is substantially positioned in the ureteral passageway 16, with the second end 88 of the kidney portion 52 being positioned in the bladder 14 near the ureter orifice 20, as shown in FIGS. 6 and 6A. The outer stent pusher 104 and the kidney portion 54 may be guided fluoroscopically by the radiopaque elements on the stent 50 and/or one the outer stent pusher 104 and/or by the tracking markers on the outer stent pusher. Additionally or alternatively, the stent 50 may be positioned using a suitable endoscope.

Figure 7:
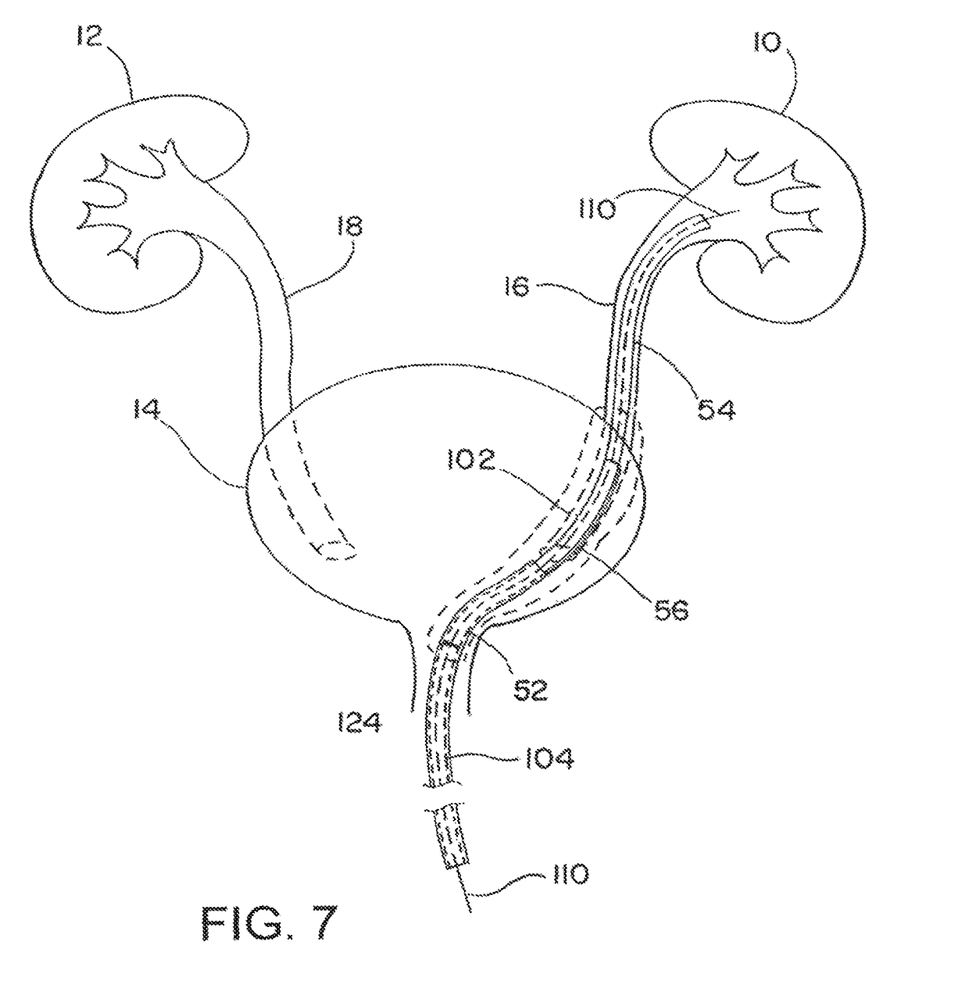
FIG. 7 is still another schematic view of the stent assembly being positioned in the patient by the stent pusher assembly.
Figure 7A:
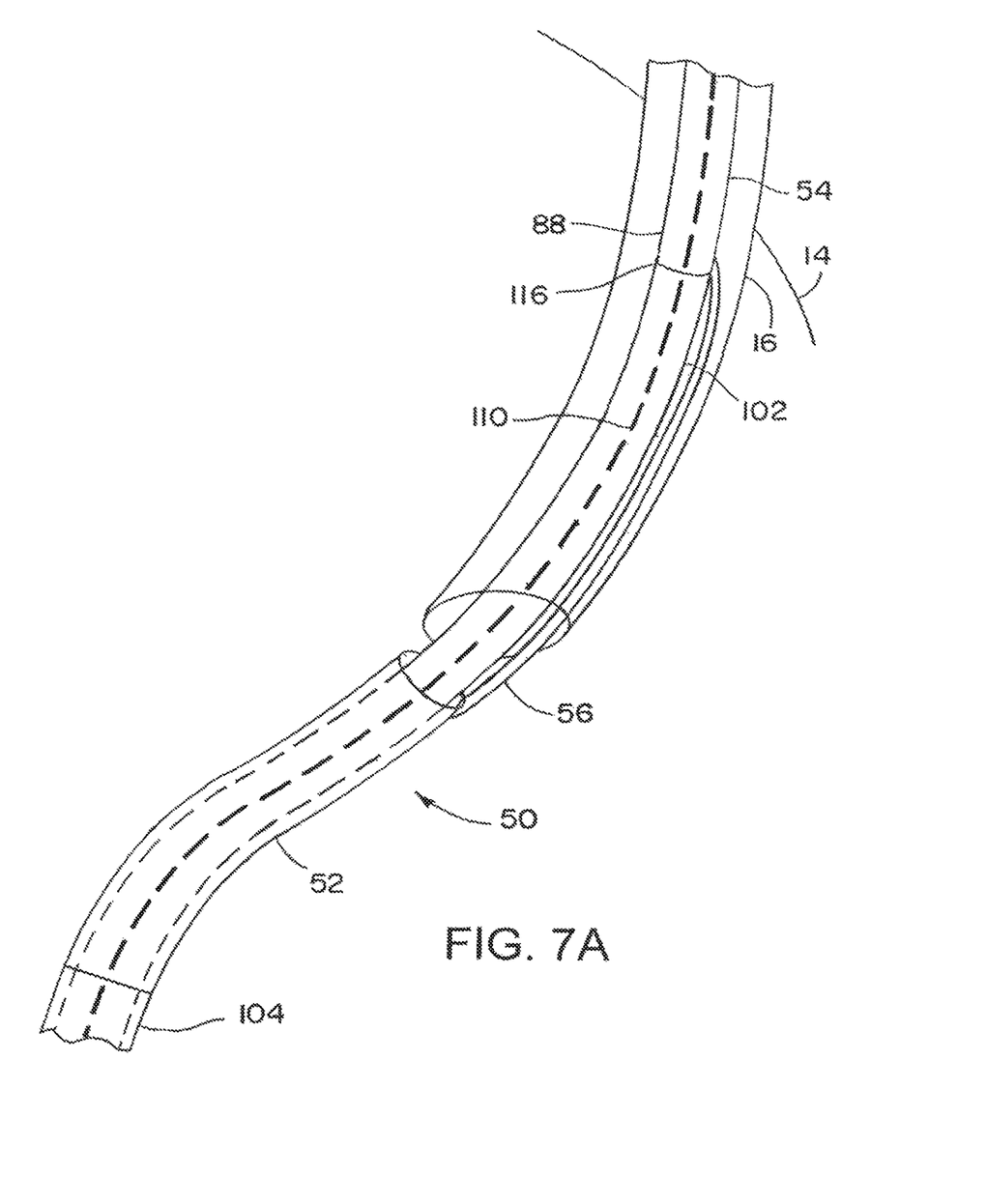
FIG. 7A is a schematic view of a blown-up portion of FIG. 7.

Next, as shown in FIGS. 7 and 7A, the inner stent pusher 102 is advanced over the guidewire 110, through the lumen 108 and through a lumen of the bladder portion 52 until a second end 116 of the inner stent pusher 102 abuts the second end 88 of the kidney portion 54. To allow the inner stent pusher 102 to advance the kidney portion 54 without inadvertently entering the lumen of the kidney portion 54, the outer diameter of the inner stent pusher 102 is equal to or greater than the outer diameter of the kidney portion 54. Additionally, as should be appreciated, the inner diameter of the bladder portion 52 is greater than the outer diameter of the kidney portion 54 to allow the inner stent pusher 102 having an outer diameter equal to or greater than the diameter of the kidney portion 54 to be advanced through the bladder portion 52.

Figure 8:
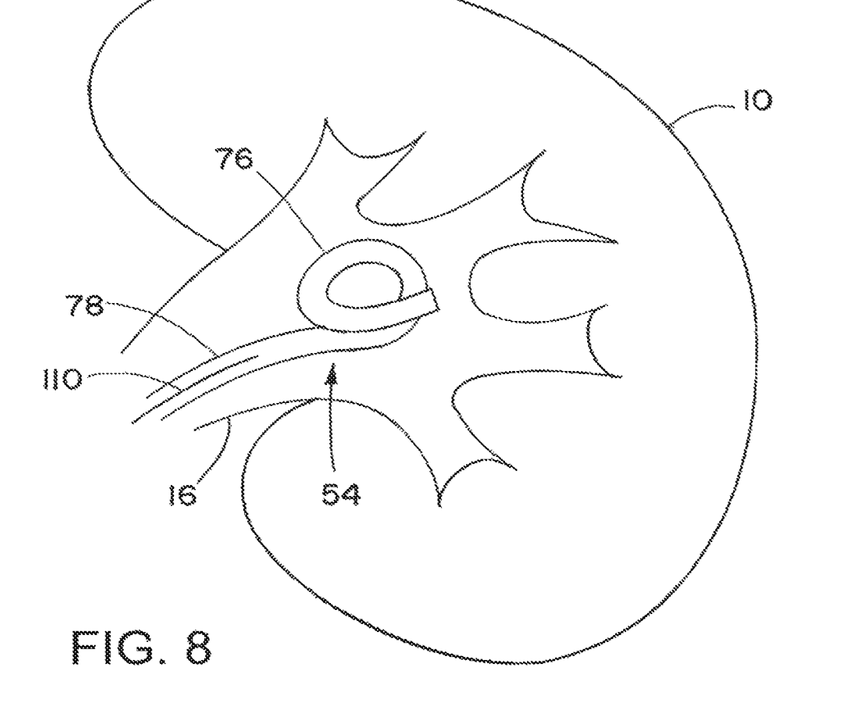
FIG. 8 is a schematic view of a kidney with a kidney portion of the stent assembly inserted therein.

The inner stent pusher 102 is then advanced to advance the kidney portion 54 further into the ureteral passageway 16. The kidney portion 54 is advanced until the second end 88 of the kidney portion 54 is positioned in the ureteral passageway 16 and the first end 86 of the kidney portion 54, i.e. the fixing portion 76, is disposed in the kidney 10. As should be appreciated, while the guidewire 110 is disposed within the kidney portion 54, the kidney portion remains in the restrained shape. After the kidney portion 54 has been positioned in the kidney 10 and ureteral passageway 16 as shown in FIGS. 6 and 7A, the guidewire 110 is withdrawn from the first end 86 of the kidney portion 54 to allow the fixing portion 76 to return to its unrestrained shape, as shown in FIG. 8. When unrestrained, the fixing portion secures the kidney portion 54 in the kidney 10, and the ureter portion 78 extends from the kidney 10 into the ureteral passageway 16 to keep the passageway open.

Figure 9:
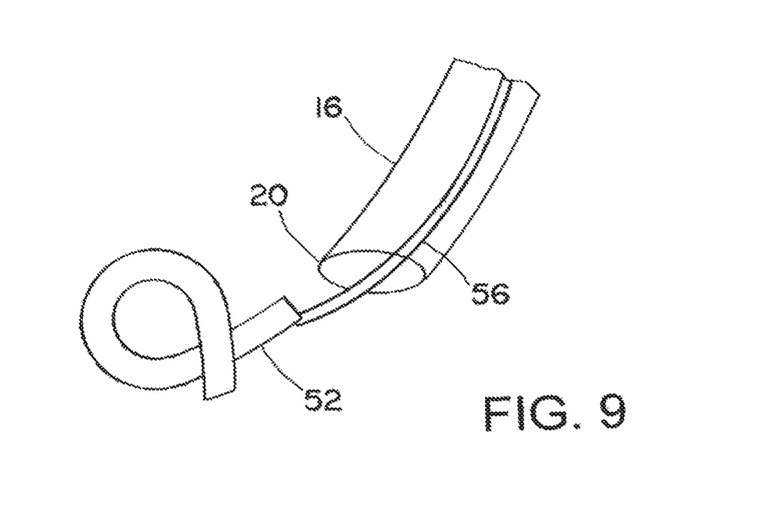
FIG. 9 is a schematic view of a ureteral passageway and bladder with a bladder portion of the stent assembly inserted therein.

The guidewire 110, inner stent pusher 102, and outer stent pusher 104 are then withdrawn from the patient, either separately, simultaneously or in any suitable order, to allow the bladder portion 52 to return to its unrestrained shape, i.e. the flexible loop as shown in FIG. 9. When unrestrained, the flexible loop prevents the bladder portion 52 from migrating into the ureteral passageway to reduce irritation of the ureter orifice 20.

Although described as being advance over the guidewire 110 after the outer stent pusher 104 has been used to advance the kidney portion 54, it will be appreciated that the inner stent pusher 102 may be advanced over the guidewire 110 at the same time as the outer stent pusher 104 and advanced into the patient at the same time or later than the outer stent pusher 104.

Although the invention has been shown and described with respect to a certain embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A method for positioning a ureteral stent in a kidney, ureteral passageway, and bladder of a patient using a stent pusher assembly having an inner and outer pusher, the ureteral stent including a bladder portion configured to be positioned in the bladder, a kidney portion configured to be positioned in the kidney and the ureteral passageway, and at least one tether coupled to the bladder portion and the kidney portion, the method including:
   advancing a guidewire into the bladder, the ureteral passageway and the kidney;
   advancing the kidney portion and bladder portion over the guidewire;
   advancing the outer pusher over the guidewire;
   advancing the outer pusher along the guidewire until a second end of the outer pusher abuts against an endmost surface of a first end of the bladder portion;
   advancing the outer pusher towards the kidney to push the bladder portion and kidney portion until the kidney portion is positioned in the ureteral passageway;
   advancing the inner pusher over the guidewire, through a lumen of the outer pusher and through a lumen of the bladder portion until a second end of the inner pusher abuts against an endmost surface of a second end or the kidney portion; and
   advancing the inner pusher towards the kidney to push the kidney portion such that the second end of the kidney portion is disposed in the ureteral passageway and a first end of the kidney portion is disposed in the kidney.

2. The method according to claim 1, wherein the kidney portion and bladder portion are in respective restrained shapes when the guidewire extends through the kidney portion and bladder portion.

3. The method according to claim 2, further including: withdrawing the guidewire from a first end of the kidney portion to allow the first end to move to an unrestrained shape to secure the kidney portion in the kidney; and withdrawing the guidewire, inner pusher and outer pusher from the bladder portion to allow the bladder portion to move to an unrestrained shape to prevent the bladder portion from migrating into the ureteral passageway.

4. The method according to claim 1, wherein advancing the outer pusher towards the kidney until the kidney portion is positioned in the ureteral passageway includes advancing the outer pusher until a portion of the kidney portion is positioned in the bladder and a majority of the kidney portion is positioned in the ureteral passageway.

5. The method according to claim 1, wherein the outer pusher has an axial length less than an axial length of the inner pusher.

6. The method according to claim 1, wherein an outer diameter of the inner pusher is equal to or greater than an outer diameter of the kidney portion to allow the inner pusher to push the kidney portion without entering a lumen of the kidney portion.

7. The method according to claim 1, wherein an inner diameter of the bladder portion is greater than an outer diameter of the kidney portion to allow the inner pusher having an outer diameter equal to or greater than the outer diameter of the kidney portion to be advanced through the bladder portion.

8. A method for positioning a ureteral stent in a kidney, ureteral passageway, and bladder of a patient using a stent pusher assembly, the ureteral stent including a bladder portion having an open proximal end, an open distal end, and a lumen extending therebetween, a kidney portion having an open proximal end, an open distal end, and a lumen extending therebetween, and at least one tether connecting the bladder portion and the kidney portion, and the stent pusher assembly including an inner stent pusher including a body having an open proximal end, an open distal end, and a lumen extending therebetween, and an outer stent pusher including a body having an open proximal end, an open distal end, and a lumen extending therebetween, wherein the body of the inner stent pusher has an axial length greater than an axial length of the body of the outer stent pusher, the method including:
   advancing a guidewire into the bladder, the ureteral passageway and the kidney;
   advancing the kidney portion and bladder portion over the guidewire;
   advancing the distal end of the outer stent pusher until the distal end abuts against the proximal end of the bladder portion while the distal end of the bladder portion abuts the proximal end of the kidney portion;
   pushing the bladder portion and kidney portion at the same time until the kidney portion is positioned in the ureteral passageway and the bladder portion is positioned in the bladder;
   advancing the inner stent pusher through the lumen of the outer stent pusher and through the lumen of the bladder portion such that the distal end of the inner stent pusher abuts against the proximal end of the kidney portion; and pushing the kidney portion into the kidney such that the bladder portion remains in the bladder.

* * * * *